US008636838B2

(12) United States Patent
Watanabe et al.

(10) Patent No.: US 8,636,838 B2
(45) Date of Patent: Jan. 28, 2014

(54) OXYGEN CONCENTRATOR

(75) Inventors: Hirofumi Watanabe, Sayama (JP); Keiichi Asakura, Sayama (JP)

(73) Assignee: Ikiken Co., Ltd., Sayama-Shi, Saitama (JP)

( * ) Notice: Subject to any disclaimer, the term of this patent is extended or adjusted under 35 U.S.C. 154(b) by 0 days.

(21) Appl. No.: 13/516,944

(22) PCT Filed: Nov. 29, 2010

(86) PCT No.: PCT/JP2010/006946
§ 371 (c)(1),
(2), (4) Date: Aug. 27, 2012

(87) PCT Pub. No.: WO2011/074192
PCT Pub. Date: Jun. 23, 2011

(65) Prior Publication Data
US 2012/0304867 A1 Dec. 6, 2012

(30) Foreign Application Priority Data

Dec. 18, 2009 (JP) .................................. 2009-288266

(51) Int. Cl.
*B01D 46/42* (2006.01)
(52) U.S. Cl.
USPC ................... 96/380; 96/108; 96/381; 96/384; 96/385; 95/128; 95/130; 128/200.24
(58) Field of Classification Search
USPC .......... 128/200.24; 95/128, 130; 96/108, 380, 96/381, 384, 385
See application file for complete search history.

(56) References Cited

U.S. PATENT DOCUMENTS 4,418,788 A  12/1983  Gorchev et al.
4,450,933 A *  5/1984  Fukuoka et al. ............... 181/229
(Continued)

FOREIGN PATENT DOCUMENTS

JP    07-310651 A    11/1995
JP    2003-235982 A   8/2003
(Continued)

OTHER PUBLICATIONS

International Search Report (PCT/ISA/210) issued on Feb. 8, 2011, by the Japanese Patent Office as the International Searching Authority for International Application No. PCT/JP2010/006946.

(Continued)

*Primary Examiner* — Christopher P Jones
(74) *Attorney, Agent, or Firm* — Buchanan Ingersoll & Rooney PC

(57) ABSTRACT

To provide an oxygen concentrator that can reduce pressure loss when suctioning raw air and that can increase the amount of suctioned raw air by an amount of reduction in pressure loss, and moreover that can reduce noise without significantly changing a basic structure of a compressor. The oxygen concentrator includes: a compressor that has a plurality of suction ports suctioning raw air and that generates compressed air by compressing suctioned raw air; a conduit through which the compressed air is sent; a silencer that has a suction side end introducing the raw air and a discharge side end discharging the raw air, with the silencer being connected with the conduit; and a plurality of connection conduits directly connecting the discharge side end of the silencer and the respective suction ports of the compressor.

3 Claims, 6 Drawing Sheets

(56) References Cited

U.S. PATENT DOCUMENTS

| | | | |
|---|---|---|---|
| 4,681,099 A * | 7/1987 | Sato et al. | 128/204.23 |
| 5,370,728 A * | 12/1994 | LaSala et al. | 95/101 |
| 5,656,068 A * | 8/1997 | Smolarek et al. | 95/101 |
| 5,658,371 A * | 8/1997 | Smolarek et al. | 95/101 |
| 5,858,062 A * | 1/1999 | McCulloh et al. | 95/8 |
| 6,702,880 B2 * | 3/2004 | Roberts et al. | 96/381 |
| 7,279,029 B2 * | 10/2007 | Occhialini et al. | 96/121 |
| 7,455,717 B2 * | 11/2008 | Sprinkle | 95/22 |
| 7,510,601 B2 * | 3/2009 | Whitley et al. | 96/121 |
| 2009/0025564 A1 * | 1/2009 | Kuwabara | 96/388 |
| 2013/0008438 A1 * | 1/2013 | Sugawara et al. | 128/202.24 |

FOREIGN PATENT DOCUMENTS

| | | |
|---|---|---|
| JP | 2005-111016 A | 4/2005 |
| JP | 2008-144714 A | 6/2008 |
| JP | 2009-183489 A | 8/2009 |

OTHER PUBLICATIONS

Office Action dated May 31, 2013, issued by the Taiwanese Patent Office in the corresponding Taiwanese Patent Application No. 099144387. (4 pages).

* cited by examiner

F I G. 1
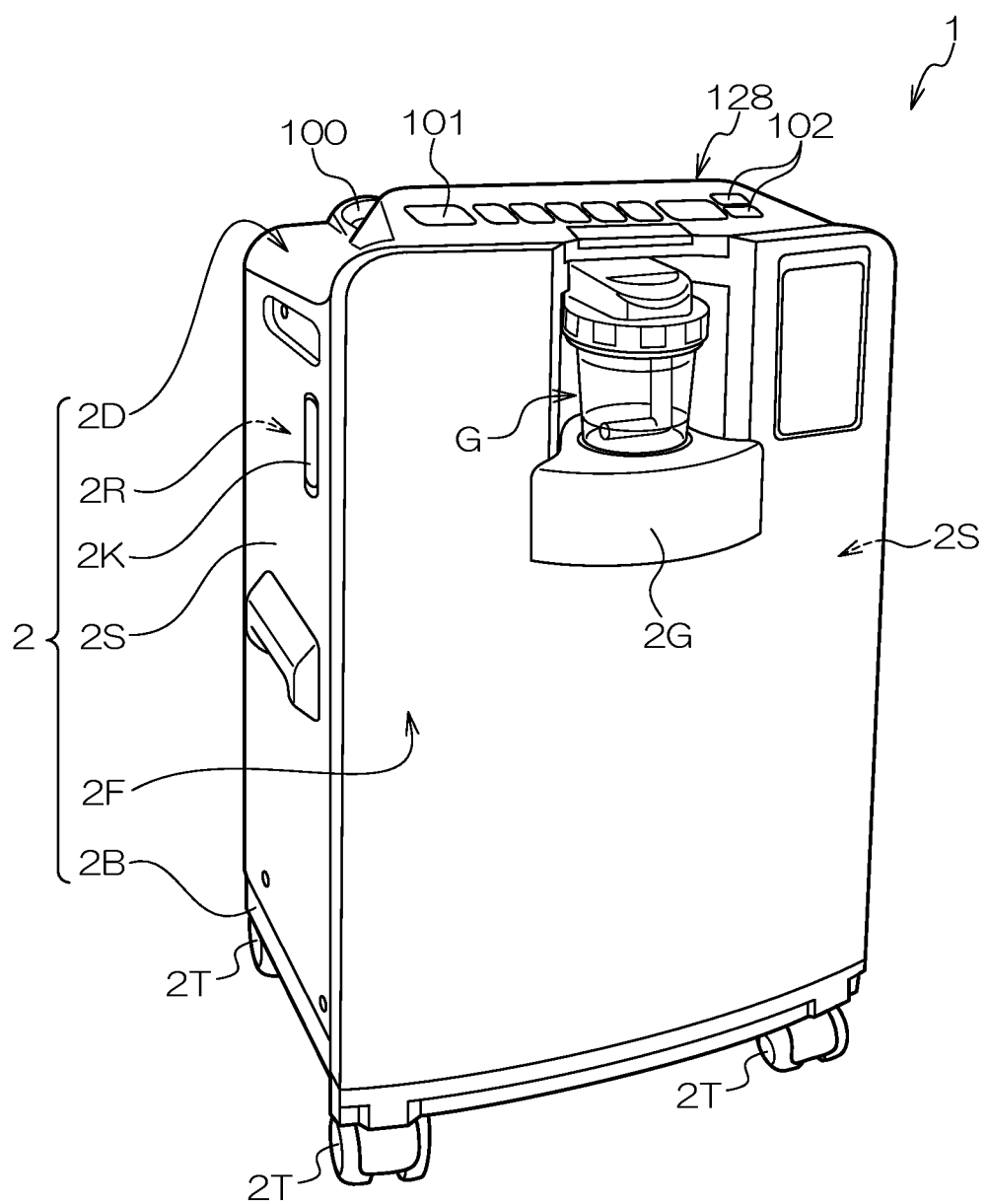

F I G.3
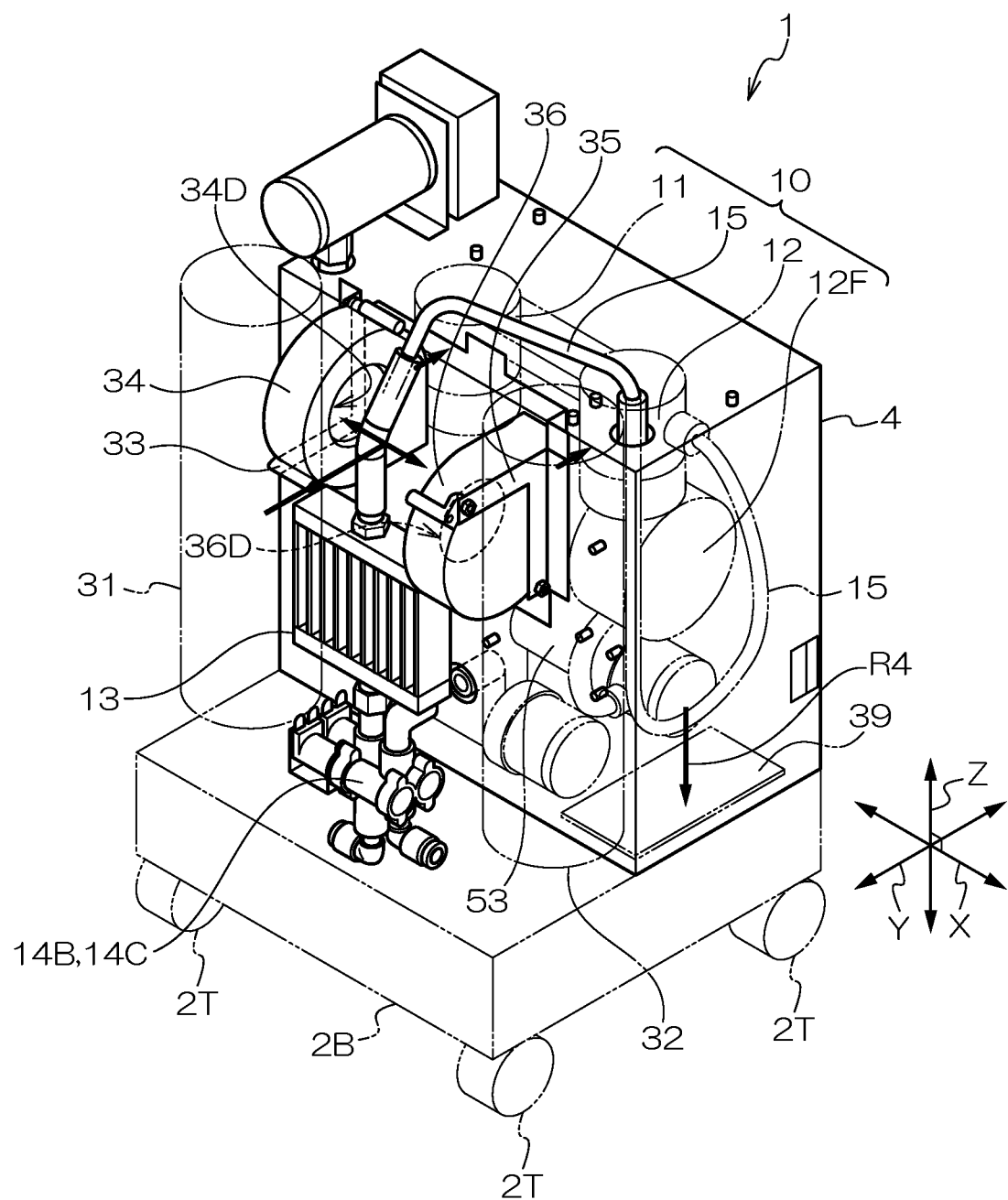

OXYGEN CONCENTRATOR

TECHNICAL FIELD

The present invention relates to an oxygen concentrator, and more particularly to a medical oxygen concentrator that is capable of supplying oxygen by compressing suctioned raw air and supplying the compressed air to an adsorbent.

BACKGROUND

An oxygen concentrator is configured to acquire oxygen by using a pressure swing adsorbing method that generates oxygen by using zeolite selectively adsorbing nitrogen by transmitting oxygen in raw air, as an adsorbent.

According to the oxygen concentrator using the method, introduced raw air is compressed by a compressor to generate compressed air and the compressed air is supplied to an adsorption column containing the adsorbent to separate oxygen by adsorbing nitrogen to the adsorbent. While the generated oxygen is stored in a tank, a predetermined flow of oxygen can be supplied from the tank through a pressure reducing valve or a flow setter to allow a patient to inhale oxygen by using a mechanism such as a nasal cannula, and the like.

When the oxygen concentrator is installed at a place where an AC power supply (utility AC power supply) can be used, for example, a domiciliary oxygen therapy patient having a deteriorated lung function can safely inhale oxygen even while sleeping to have a good sleep. In particular, when the domiciliary oxygen therapy patient uses the oxygen concentrator even while sleeping, the oxygen concentrator preferably operates very quietly. For example, noise of the oxygen concentrator is preferably equal to or less than a noise level generated from an indoor air-conditioning facility.

The oxygen concentrator used for a long-term oxygen inhalation therapy which is effective as a therapeutic method for a patient who suffers from respiratory disease, such as chronic bronchitis and the like, is generally not transportable and is not configured for the patient to take with them to go outside.

When the patient is forced to go outside, for example, the patient inhales concentrated oxygen from an oxygen bomb while pushing a cart mounted with the oxygen bomb in which oxygen is charged in a predetermined receiving reservoir. Oxygen needs to be charged in the oxygen bomb by using an exclusive facility. Therefore, a transportable or movable oxygen concentrator is proposed, and the transportable or movable oxygen concentrator includes a compressor that introduces raw air to generate compressed air and decompressed air (see Patent Literature 1).

CITATION LIST

Patent Literature

Patent Literature 1: Japanese Patent Application Laid-Open No. 2005-111016

SUMMARY OF INVENTION

Technical Problem

However, in a conventional oxygen concentrator, as illustrated in FIG. 6, one conduit 401, and a branch conduit 404 and a branch conduit 405 formed by branching the midstream of the conduit 401 are placed around a compressor 400. The branch conduits 404 and 405 are connected to two intake ports 402 for raw air of the compressor 400, respectively. A silencer 403 is set to reduce noise at midstream of the conduit 401. The raw air is supplied to two intake ports 402 of the compressor 400 through the conduit 401, the silencer 403, and the branch conduits 404 and 405 of the conduit 401.

However, when the raw air is transported from the conduit 401 to the branch conduits 404 and 405 in order to increase the amount of suctioned raw air, pressure loss is increased, and as a result, the actual amount of suctioned raw air is decreased.

Accordingly, an object of the present invention is to provide an oxygen concentrator that can reduce pressure loss when suctioning raw air and increase an amount of suctioned raw air by an amount of reduction in the pressure loss without significantly changing a basic structure of a compressor.

Solution to Problem

An oxygen concentrator according to the present invention includes: a compressor that has a plurality of suction ports suctioning raw air and that generates compressed air by compressing the suctioned raw air; and a silencer installed at a stage preceding the compressor to reduce noise from the suction ports, in which the plurality of suction ports of the compressor are individually connected with the silencer.

According to the configuration, by directly connecting the plurality of raw air suction ports of the compressor to the silencer by using respective connection conduits, the amount of sent raw air per one connection conduit can be reduced and the raw air can be introduced into the compressor without loss by reducing pressure loss.

In the oxygen concentrator of the present invention, the compressor may include a first pump unit and a second pump unit that respectively generate the compressed air by compressing the raw air by reciprocatively moving a piston in a sleeve, and the suction ports may be formed in the first pump and the second pump unit, respectively.

According to the configuration, since a raw air suction port of the first pump unit and the raw air suction port of the second pump can be directly connected by using the respective connection conduits, the influence of the pressure loss can be reduced by reducing the amount of sent raw air per one connection conduit.

In the oxygen concentrator of the present invention, the silencer may have a filter removing dust in the compressed air.

According to the configuration, after the filter removes the dust in the compressed air, the compressed air can be sent to the plurality of connection conduits and the influence of the pressure loss can be reduced by reducing the amount of sent raw air per one connection conduit.

Advantageous Effects of Invention

According to the present invention, it is possible to provide an oxygen concentrator that can reduce pressure loss when suctioning raw air and increase an amount of suctioned raw air by an amount of reduction in the pressure loss without significantly changing a basic structure of a compressor.

BRIEF DESCRIPTION OF THE DRAWINGS

FIG. 1 is a perspective view viewed from the front side, which illustrates an exterior of an embodiment of an oxygen concentrator with a compressor of the present invention.

FIG. 3 is a perspective view diagonally viewed from the rear side, which illustrates an internal structure example of the oxygen concentrator illustrated in FIGS. 1 and 2.

DESCRIPTION OF EMBODIMENTS

Hereinafter, an exemplary embodiment of the present invention will be described in detail with reference to the accompanying drawings.

Figure 2:
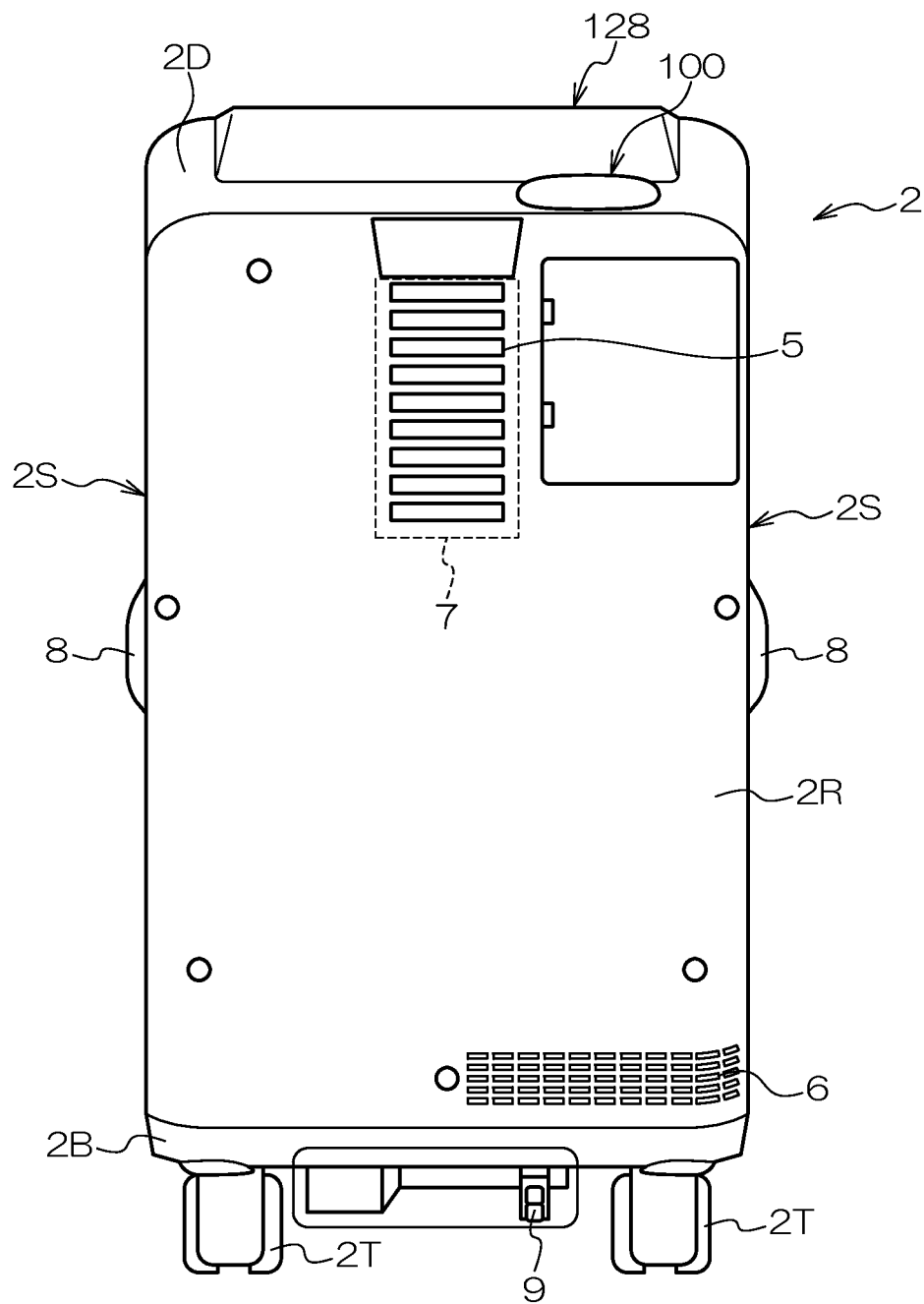
FIG. 2 is a bottom view of the exterior of the oxygen concentrator of FIG. 1.

FIG. 1 is a front perspective view illustrating an exterior of an embodiment of an oxygen concentrator with a compressor of the present invention. FIG. 2 is a bottom view of the exterior of the oxygen concentrator of FIG. 1.

The oxygen concentrator 1 illustrated in FIGS. 1 and 2 is preferably a portable (also called transportable or movable) oxygen concentrator. The oxygen concentrator 1 illustrated in FIG. 1 uses for example, compressed air pressure swing adsorption (PSA) by compressed air as an oxygen generation principle.

The oxygen concentrator 1 illustrated in FIGS. 1 and 2, which is an oxygen concentrator having an oxygen flow of maximum 5 L class as one example, has a height of approximately 630 mm, a width of approximately 350 mm, an inner length of approximately 300 mm, and a weight of 21 to 23 kg, and a setting unit of the oxygen flow is set to be in the range of for example, 0.25 to 5 L. The oxygen concentrator 1 includes a substantially rectangular parallelepiped main case 2, a display unit 128 capable of setting a flow, a humidifier G, a cannular rack 2K, and casters 2T positioned at four edges.

The main case 2 includes a front panel 2F, left and right side panels 2S, and a rear panel 2R, a top 2D, and a bottom 2B. In an inner surface of the main case 2, as a soundproof material, a non-woven fabric, which consists of a polyolefin based fiber (preferably, a polypropylene fiber) having a fiber diameter in the range of 1 to 4 µm and a polyolefin based fiber (preferably, a polypropylene fiber) having a fiber diameter in the range of 20 to 30 µm, may be used. By using the non-woven fabric, a light weight and a soundproof effect are achieved. As illustrated in FIG. 1, the display unit 128, an oxygen outlet 100, a power switch 101, and an oxygen flow setting button 102 are placed on the top 2D. A placement section 2G of the humidifier G is installed in an upper part of the front panel 2F. The casters 2T are placed at four edges of the bottom 2B and the oxygen concentrator 1 is movable by using the casters 2.

Referring to FIG. 2, in the rear panel 2R, an air introduction port 5 for introducing outdoor air into the main case 2 is formed at a central position of an upper part of the rear panel 2R and an exhaust port 6 for discharging warmed air in the main case 2 to the outside is formed at a lower right part of the rear panel 2R. An air introduction port filter 7 is removably mounted on an inner surface of the air introduction port 5. In addition, the left and right side panels 2B have handles 8 and the bottom 2B has a retractable power cord 9.

Figure 4:
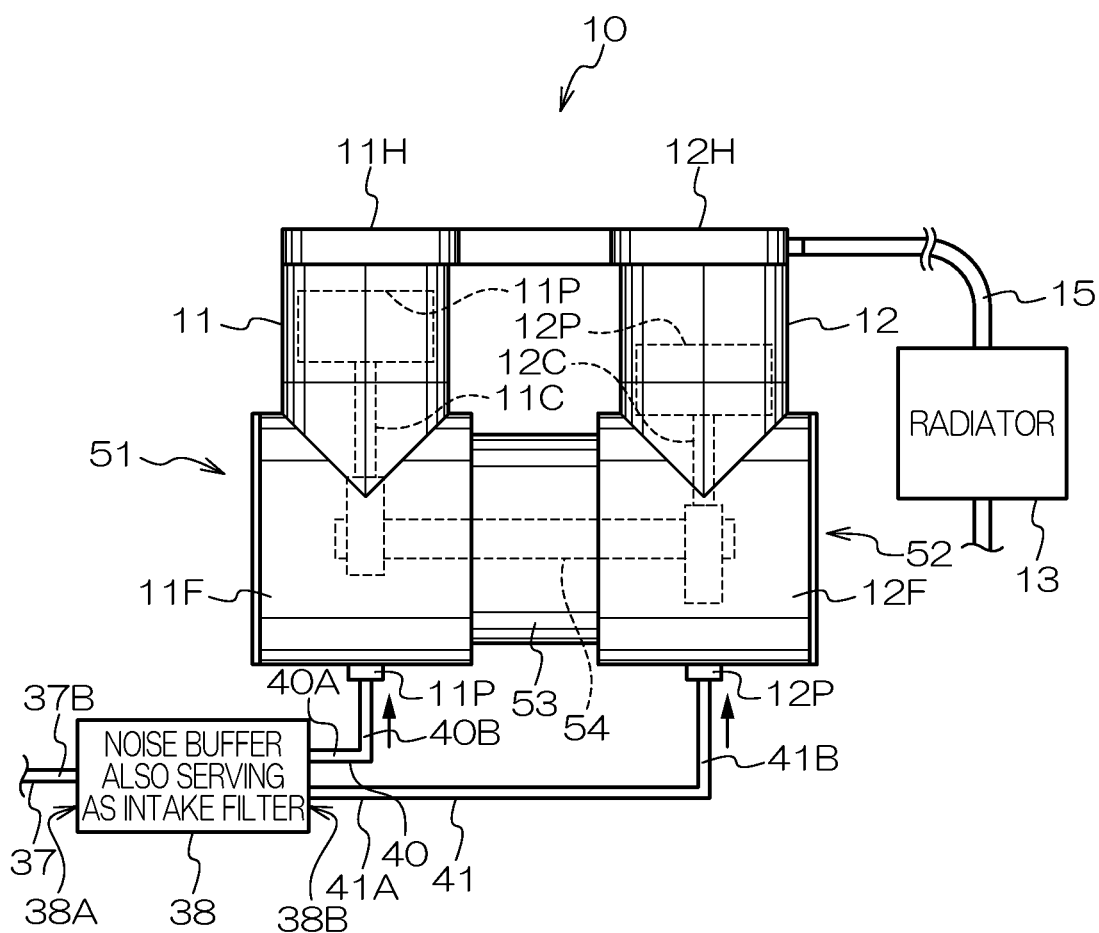
FIG. 4 is a diagram illustrating a compressor, a first connection conduit and a second connection conduit connected to the compressor, and a noise buffer also serving as an intake filter.

FIG. 3 is a perspective view illustrating an internal structure example of the oxygen concentrator 1 illustrated in FIGS. 1 and 2, which is diagonally viewed from the rear side. FIG. 4 is a diagram illustrating a horizontally-opposed compressor 10, a first connection conduit 40 and a second connection conduit 41 connected to the compressor 10, and a noise buffer 38 also serving as an intake filter. The first connection conduit 40 and the second connection conduit 41 are made of a thermoplastic resin, for example, polyurethane for easy handling at the time of installation and have an inner diameter in the range of 4 to 6 mm, an outer diameter in the range of 7 to 9 mm, and a wall thickness in the range of 1.3 to 2.0 mm, and preferably, have an inner diameter of 5 mm, an outer diameter of 8 mm, and a wall thickness of 1.5 mm. When the outer diameter is larger than 9 mm, a warpage radius is increased while handling, when the inner diameter is smaller than 4 mm, pressure loss is increased, and when the wall thickness is smaller than 1.3 mm, bending (kink) becomes easy while handling. As illustrated in FIG. 3, the compressor 10 is set on the bottom 2B and the compressor 10 is placed in a rectangular parallelepiped compressor case 4 for sound proofing. In an inner surface of the compressor case 4, as the soundproof material, a non-woven fabric, which consists of a polyolefin based fiber (preferably, a polypropylene fiber) having a fiber diameter in the range of 1 to 4 µm and a polyolefin based fiber (preferably, a polypropylene fiber) having a fiber diameter in the range of 20 to 30 µm, maybe used. By using the non-woven fabric, a light weight and a soundproof effect are achieved. On a bottom surface of the compressor case 4, a first adsorption column body 31 and a second adsorption column body 32 are fixed while standing at an interval in an X direction and in parallel in a Z direction (vertical direction).

As illustrated in FIG. 3, a sleeve 12 of the compressor 10 is connected to a conduit 15 and a cooling radiator 13 and 3-way switching valves 14B and 14C are connected to the midstream of the conduit 15. A first fan 34 is mounted inside the first adsorption column body 31 and a second fan 36 is mounted inside the second adsorption column body 32.

As illustrated in FIG. 3, as the first fan 34 and the second fan 36 that have the same shape, for example, a sirocco fan is used and the first and second fans 34 and 36 are positioned to face each other, but the first and second fans 34 and 36 are fixed such that the first and second fans 34 and 36 are mounted in vertically opposite directions to each other and face each other.

As illustrated in FIG. 3, the cooling radiator 13 is placed below the first fan 34 and the second fan 36, between the first adsorption column body 31 and the second adsorption column body 32. A power control circuit 39 is placed on the bottom 2B.

FIG. 4 is a diagram illustrating a structure example of the compressor 10 and the compressor 10 includes a first pump unit 51 and a second pump unit 52. The first pump unit 51 includes a cylindrical sleeve 11, a piston 11P placed in the sleeve 11, a head cover 11H, a con rod 11C, and a case section 11F. Similarly, the second pump unit 52 includes a cylindrical sleeve 12, a piston 12P placed in the sleeve 12, a head cover 12H, a con rod 12C, and a case section 12F.

As illustrated in FIG. 4, the sleeves 11 and 12 are also called piston cylinders. A driving motor 53, which is for example, asynchronous motor, has an output shaft 54. Con rods 11C and 12C are rotatably supported on both ends of the output shaft 54.

As illustrated in FIG. 4, the noise buffer (silencer) 38 also serving as the intake filter is placed among the conduit 37, and the first connection conduit 40 and the second connection conduit 41. The first connection conduit 40 and the second connection conduit 41 are made of a thermoplastic resin, for example, polyurethane for easy handling at the time of installation and have an inner diameter in the range of 4 to 6 mm, an outer diameter in the range of 7 to 9 mm, and a wall thickness in the range of 1.3 to 2.0 mm, and preferably, have an inner diameter of 5 mm, an outer diameter of 8 mm, and a wall thickness of 1.5 mm. When the outer diameter is larger than 9 mm, the warpage radius is increased while handling, when the inner diameter is smaller than 4 mm, the pressure loss is increased, and when the wall thickness is smaller than 1.3 mm, the bending (kink) becomes easy while handling.

An end 37B of the conduit 37 is connected to a suction side end 38A of the noise buffer 38 also serving as the intake filter, and a first end 40A of the first connection conduit 40 and a first end 41A of the second connection conduit 41 are connected to a discharge side end 38B of the noise buffer 38 also serving as the intake filter. A second end 40B of the first connection conduit 40 is connected to a suction port 11P of the case section 11F and a second end 41B of the second connection conduit 41 is connected to a suction port 12P of the case section 12F.

An introduction path of the raw air between the noise buffer 38 also serving as the intake filter and the compressor 10 is divided into a plurality of paths, and the first connection conduit 40 and the second connection conduit 41 are connected in parallel between the noise buffer 38 also serving as the intake filter and the compressor 10. In other words, the first connection conduit 40 and the second connection conduit 41 directly connect the suction ports 11P and 12P of the noise buffer 38 also serving as the intake filter and the compressor 10.

As a result, as the raw air introduced from the conduit 37 into the noise buffer 38 also serving as the intake filter passes through the noise buffer 38 also serving as the intake filter, dust is removed by the intake filter, and after noise is reduced, the raw air flows dividedly into the first connection conduit 40 and the second connection conduit 41 and may be introduced into the case section 11F through the suction port 11P of the case section 11F and further, may be introduced into the case section 12F through the suction port 12P of the case section 12F.

The head covers 11H and 12H are commonly connected to the conduit 15 and the generated compressed air is sent through the conduit 15. A heat-dissipating radiator 13 is placed at midstream of the conduit 15.

Herein, as the connection conduits, two conduits, that is, the first connection conduit 40 and the second connection conduit 41, are installed in the embodiment, but the connection conduits are installed as many as sleeves (cylinders) and when the number of the sleeves increases, individually connected connection conduits are also correspondingly increased as many.

Herein, referring to FIG. 5, a system configuration example of the oxygen concentrator 1 as described above will be described.

Figure 5:
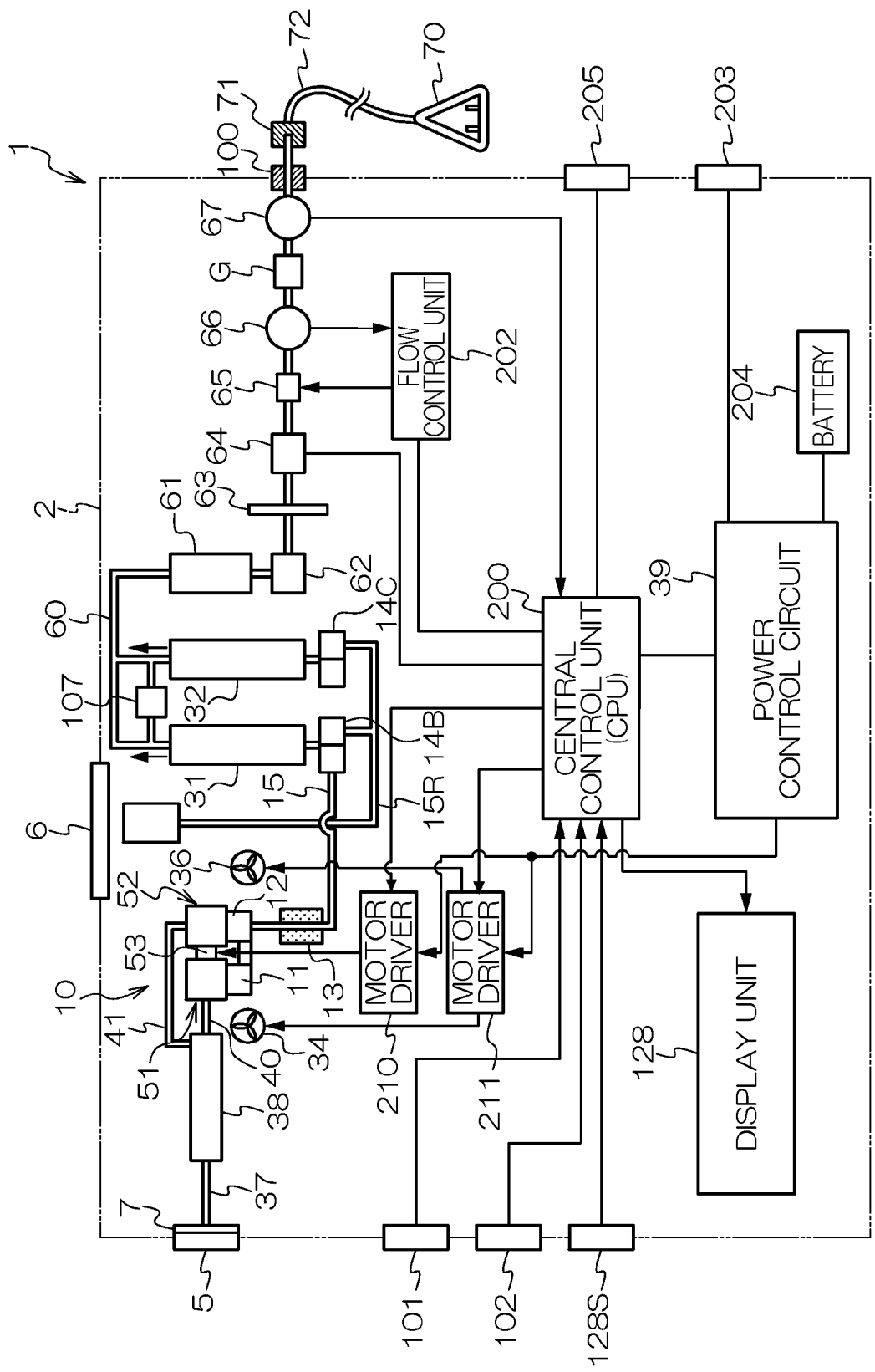
FIG. 5 is a diagram illustrating a system configuration example of the oxygen concentrator.

FIG. 5 is a diagram illustrating the system configuration example of the oxygen concentrator 1.

A double line illustrated in FIG. 5 represents a conduit serving as a path for the raw air, oxygen gas, and nitrogen gas. A thin solid line represents a wire for power supplying or an electrical signal. The main case 2 of the oxygen concentrator 1 illustrated in FIG. 5 is represented by a dashed line and the main case 2 is an airtight container that hermetically seals components placed therein.

As illustrated in FIG. 5, the main case 2 includes the air introduction port 5 for introducing raw air as outdoor air, the air introduction port filter 7 and the exhaust port 6 for exhausting raw air. The air introduction port filter 7 for removing impurities such as dust, and the like in the air is replaceably placed at the air introduction port 5. When the compressor 10 operates, the raw air is introduced into the compressor 10 through the internal conduit 37, the noise buffer 38 also serving as the intake filter, and the first connection conduit 40 and the second connection conduit 41 connected to the noise buffer 38 also serving as the intake filter in parallel via the air introduction port filter 7.

As such, the raw air is introduced into the compressor 10 to become the compressed air, but heat is generated when the raw air is compressed. As a result, the compressor 10, in particular, the sleeves 11 and 12 are cooled by blowing from the first fan 34 and the second fan 36 for cooling. The compressed air sent from the compressor 10 through the conduit 15 is cooled by the radiator 13.

By cooling the compressed air, the temperature of zeolite as an adsorbent of which a function deteriorates at high temperature may be prevented from being increased. As a result, zeolite may sufficiently serve as the adsorbent for generating oxygen by adsorption of nitrogen and oxygen may be concentrated up to approximately 90% or more.

The first adsorption column body 31 and the second adsorption column body 32 as examples of adsorption members placed in line are placed in parallel vertically. The 3-way switching valves 14B and 14C are connected to the first adsorption column body 31 and the second adsorption column body 32, respectively. One end of one 3-way switching valve 14B is connected to the conduit 15. One 3-way switching valve 14B and the other 3-way switching valve 14C are connected to each other and one end of the other 3-way switching valve 14C is connected to a conduit 15R. An end of the conduit 15R reaches the exhaust port 6.

The 3-way switching valves 14B and 14C are connected to correspond to the first adsorption column body 31 and the second adsorption column body 32, respectively. The compressed air generated from the compressor 10 are alternately supplied to the first adsorption column body 31 and the second adsorption column body 32 through the conduit 15, and the 3-way switching valves 14B and 14C.

Zeolite as a catalyst adsorbent is stored in each of the first adsorption column body 31 and the second adsorption column body 32. The zeolite is X-type zeolite in which for example, a ratio of $Si_2O_3/Al_2O_3$ is in the range of 2.0 to 3.0, and zeolite in which at least 88% of a tetrahedral unit of $Al_2O_3$ is combined with lithium cation is used to increase an adsorption amount of nitrogen per unit weight. The zeolite has particularly, a granule measurement value which is less than 1 mm and at least 88% of the tetrahedral unit is preferably fused with lithium cation. By using zeolite, the amount of used raw air required to separate oxygen may be reduced as compared with a case of using other adsorbent. As a result, the compressor 10 for generating the compressed air may be further miniaturized and low noise of the compressor 10 may be achieved.

As illustrated in FIG. 5, a uniform-pressure valve 107 constituted by a check valve, a diaphragm valve, and an opening/closing valve is connected to outlets of the first adsorption column body 31 and the second adsorption column body 32. A joined conduit 60 is connected to a downstream side of the uniform-pressure valve 107 and a buffer 61 is connected to the conduit 60. The buffer 61 is an oxygen storing container for storing oxygen having a concentration of approximately 90% or more which is separately generated from the first adsorption column body 31 and the second adsorption column body 32.

As illustrated in FIG. 5, a pressure adjuster 62 is connected to a downstream side of the buffer 61 and the pressure adjuster 62 is a regulator that automatically adjusts the pressure of oxygen at an outlet of the buffer 61 to be uniform. A zirconia or ultrasonic oxygen concentration sensor 64 is connected to a downstream side of the pressure adjuster 62 through a filter 63 and the oxygen concentration sensor 64 detects the concentration of oxygen intermittently (every 10 to 30 minutes) or continuously.

As illustrated in FIG. 5, a proportional opening rate valve 65 is connected to the buffer 61. The proportional opening rate valve 65 is opened/closed in link with setting button operation of the oxygen flow setting button 102 by a signal from a flow control unit 202 according to a command of a central control unit 200. An oxygen flow sensor 66 is connected to the proportional opening rate valve 65. The humidifier G and an oxygen flow sensor 67 are connected to the oxygen flow sensor 66. The oxygen outlet 100 is connected to a stage subsequent to the oxygen flow sensor 67.

A coupler socket 71 of a nasal cannula 70 is removably connected to the oxygen outlet 100. The coupler socket 71 is connected to the nasal cannula 70 through a tube 72. A patient may inhale for example, oxygen having a flow corresponding to a maximum flow of 5 L/min. and concentrated at approximately 90% or more, through the nasal cannula 70.

Subsequently, a power system will be described with reference to FIG. 5.

A connector 203 of an AC (utility AC) power supply illustrated in FIG. 5 is electrically connected to the power control circuit 39 and the power control circuit 39 rectifies AC voltage of the utility AC power supply into predetermined DC voltage. A built-in battery 204 is built in the main case 2. The built-in battery 204 is a secondary battery which is repeatedly rechargeable and the built-in battery 204 may be recharged by receiving power supplied from the power control circuit 39.

As a result, the central control unit 200 of FIG. 1 controls the power control circuit 39, such that the power control circuit 39 may be, for example, used while being automatically switched to any one supply state of a first power supply state in which the power control circuit 39 operates by receiving power supplied from an AC adapter 203 and a second power supply state in which the power control circuit 39 operates by receiving power supplied from the built-in battery 204. As the built-in battery 204, a lithium ion secondary battery and a lithium hydrogen ion secondary battery, which are low in memory effect while charging and are fully charged even while recharging, may be used, but a nickel cadmium battery or a nickel hydrogen battery in the related art may be used.

The central control unit 200 of FIG. 5 is electrically connected to a motor driver 210 and a fan motor driver 211. The central control unit 200 stores a program to switch an operation mode to an optimal operation mode depending on the amount of separated oxygen. The motor driver 210 and the fan motor driver 211 control to automatically drive the compressor 10, and the first fan 34 and the second fan 36 at a high speed when a large amount of oxygen is generated and to rotatably drive the compressor 10, and the first fan 34 and the second fan 36 at a low speed when a small amount of oxygen is generated, according to the command of the central control unit 200.

A read only memory (ROM) storing a predetermined operation program is built in the central control unit 200 and a circuit constituted by an external storage device, a volatile memory, a temporary storage device, and a real-time clock is electrically connected to the central control unit 200. The central control unit 200 is accessible by connecting with an external communication line, and the like through a communication connector 205.

By on/off-controlling the 3-way switching valves 14B and 14C and the uniform-pressure valve 107 illustrated in FIG. 5, a control circuit (not illustrated) that controls unnecessary gas in the first adsorption column body 31 and the second adsorption column body 32 to be desorbed, the pressure adjuster 62, the flow control unit 202, and the oxygen concentration sensor 64 are electrically connected to the central control unit 200. The flow control unit 202 controls the proportional opening rate valve 65, and oxygen flow values of the oxygen flow sensor 66 and the oxygen flow sensor 67 are sent to the central control unit 200. The oxygen flow setting button 102, the display unit 128, and the power switch 101 are electrically connected to the central control unit 200 illustrated in FIG. 5.

The oxygen flow setting button 102 may set the flow of oxygen whenever for example, operating oxygen concentrated at approximately 90% or more from 0.25 L (liter) to the maximum 5 L by 0.25 L per minute. As the display unit 128, for example, a display device such as a liquid crystal monitor displaying 7 segments, and the like is used. For example, display items including the oxygen flow, an oxygen lamp, warning icons (tube bending, separation of the humidifier, decrease in oxygen concentration, stoppage of power supplying, a residual quantity of the battery, battery in operation, and a charging lamp), an accumulation time, and the like may be displayed in the display unit 128.

The compressor 10 illustrated in FIG. 5 generates only the compressed air to send the compressed air to the first adsorption column body 31 and the second adsorption column body 32 by static pressure swing adsorption (PSA) and adsorbs nitrogen in the compressed air by the adsorbent in the first adsorption column body 31 and the second adsorption column body 32, as already described. Although the driving motor 53 of the compressor 10 is the synchronous motor, the driving motor 53 may be other motors, for example, a single phase AC induction motor or a single phase 4-pole AC synchronous motor and is not particularly limited to a specific type.

Subsequently, an operation example of the oxygen concentrator 1 will be described.

The central control unit 200 illustrated in FIG. 5 gives a command to the motor driver 210 to allow the motor driver 210 to start the driving motor 53 of the compressor 10, thus consecutively rotating the output shaft 54 of the driving motor 53 illustrated in FIG. 7. As a result, a piston 11P of a first head section 51 and a piston 12P of a second head section 52 illustrated in FIG. 7 move reciprocatively.

When the compressor 10 operates, the raw air is introduced from the air introduction port 5 illustrated in FIG. 5 and the impurities such as dust are removed by the filter 7. Thereafter, the raw air is introduced into the sleeves 11 and 12 via the suction ports 11P and 12P of the compressor 10, through the internal conduit 37, the noise buffer 38 also serving as the intake filter, and the first connection conduit 40 and the second connection conduit 41 connected in parallel. As such, as the raw air introduced from the conduit 37 illustrated in FIG. 4 into the noise buffer 38 also serving as the intake filter passes through the noise buffer 38 also serving as the intake filter, dust and the like is removed, and after noise is reduced, the raw air flows dividedly into the first connection conduit 40 and the second connection conduit 41 connected in parallel and may be introduced into the case section 11F through the suction port 11P of the case section 11F and further, may be introduced into the case section 12F through the suction port 12P of the case section 12F. When the piston 11P and the piston 12P of FIG. 4 are positioned at top dead points, the raw air in the sleeve 11 and the sleeve 12 is compressed. On the contrary, when the piston 11P and the piston 12P are positioned at bottom dead points, the raw air is suctioned into the sleeve 11 and the sleeve 12.

The first connection conduit 40 and the second connection conduit 41 divide an introduction path of the raw air between the noise buffer 38 also serving as the intake filter and the compressor 10 into a plurality of systems to be parallel and directly connect the noise buffer 38 also serving as the intake filter and the suction ports 11P and 12P of the compressor 10 to each other. As a result, the amount of raw air which should be sent per one of the first connection conduit 40 and the second connection conduit 41 maybe reduced. In other words, although the diameters of the first conduit 40 and the second conduit 41 are set to be small, the pressure loss is not increased.

The compressed air generated by the compressor 10 illustrated in FIG. 5 may be supplied to the first adsorption column body 13 and the second adsorption column body 32 through the conduit 15.

Meanwhile, the central control unit 200 illustrated in FIG. 5 gives a command to the motor driver 211 to rotate the first fan 34 and the second fan 36. When the compressor 10 compresses the raw air to generate the compressed air, the sleeves 11 and 12 of the compressor 10 are cooled by blowing from the first fan 34 and the second fan 36, respectively and the compressed air that passes through the conduit 15 is cooled by passing through the radiator 13. The compressed air adsorbs nitrogen by passing through the adsorbent in the first adsorption column body 31 and the second adsorption column body 32 through the conduit 15 and the 3-way switching valves 14B and 14C, such that oxygen is separated and generated from the compressed air. The buffer 61 may store oxygen having a concentration of approximately 90% or more which is separated and generated.

The oxygen concentration sensor 66 of FIG. 5 detects the concentration of oxygen from the buffer 61. The proportional opening rate valve 65 is opened/closed in link with the oxygen flow setting button 102. Oxygen is supplied to the nasal cannula 70 through the oxygen outlet 100. As a result, the patient may inhale oxygen concentrated at approximately 90% or more at the maximum flow of, for example, 5 L/min through the nasal cannula 70.

Figure 6:
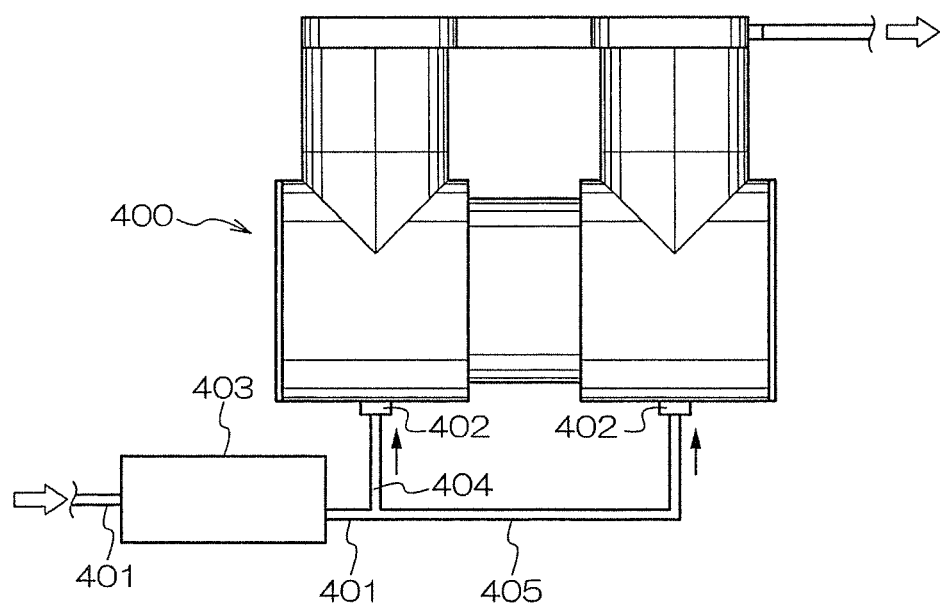
FIG. 6 is a diagram illustrating connection of a compressor and conduits in the related art.

In a connection structure of branch conduits 404 and 405 of the compressor 400 in the related art, which is illustrated in FIG. 6, when the output shaft of the driving motor is rotated at 2,200 rpm, compressed air of 61 L may be generated and electric energy used at that time is 231 Wh. On the other hand, in the embodiment of the oxygen concentrator of the present invention described above, when the driving motor 53 of the compressor 10 is rotated at 2,100 rpm, the compressed air of 61 L may be generated similarly and the electric energy used at that time is 222 Wh. That is, in order to generate the compressed air in the same quantity, 61 L, the number of rotations in the embodiment of the present invention may be decreased as compared with the related art by 100 rpm (2,200 rpm-2,100 rpm) and power consumption may also be decreased by 9 Wh (231-222). Therefore, the number of used rotations of the compressor 10 is reduced and power consumption is reduced. In other words, in the embodiment of the present invention, when the same number of rotations is maintained, more compressed air may be generated than the related art.

However, the present invention is not limited to the embodiment and various modifications and changes of the present invention can be made and various transformations can be made within the scope of the appended claims.

The illustrated compressor 10 includes the first pump unit 51 and the second pump unit 52, but is not limited thereto and may include one pump unit or three or more pump units. Fans that cool the compressor 10 may be placed such that the number of fans corresponds to the number of pumps. The driving motor of the illustrated compressor 10 is for example, the 5 L-class motor, but is not limited thereto and may adopt for example, a motor suitable for 3 L class and the like. The type of the compressor is not particularly limited and may adopt a predetermined type.

Reference Signs List

1: Oxygen concentrator
2: Main case
2F: Front panel
2S: Side panel
2R: Rear panel
2D: Top
2B: Bottom
5: Air introduction port
6: Exhaust port
10: Compressor
11: One sleeve
12: The other sleeve
11P, 12P: Piston
13: Radiator
15: conduit
31: First adsorption column body
32: Second adsorption column body
34: First fan
36: Second fan
38: Noise buffer (silencer) also serving as intake filter
40: First connection conduit
42: Second connection conduit
51: First pump unit
52: Second pump unit

The invention claimed is:

1. An oxygen concentrator, comprising:
a compressor that has a plurality of suction ports suctioning raw air and that generates compressed air by compressing the suctioned raw air; and
a silencer installed at a stage preceding the compressor to reduce noise from the suction ports,
wherein the plurality of suction ports of the compressor are individually connected with the silencer.

2. The oxygen concentrator of claim 1, wherein
the compressor includes a first pump unit and a second pump unit that respectively generate the compressed air by compressing the raw air by reciprocatively moving a piston in a sleeve, and
the suction ports are formed in the first pump and the second pump unit, respectively.

3. The oxygen concentrator of claim 1, wherein the silencer has a filter removing dust in the compressed air.

* * * * *